United States Patent
Audet et al.

(10) Patent No.: US 10,213,115 B2
(45) Date of Patent: *Feb. 26, 2019

(54) METHOD AND APPARATUS TO DETECT ISCHEMIA WITH A PRESSURE SENSOR

(71) Applicant: Medtronic, Inc., Minneapolis, MN (US)

(72) Inventors: Sarah A Audet, Shoreview, MN (US); James K Carney, Roseville, MN (US); William J Combs, Galena, OH (US); Tommy D Bennett, Shoreview, MN (US); Barbro M. L. Kjellstrom, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 135 days.

This patent is subject to a terminal disclaimer.

(21) Appl. No.: 15/090,105

(22) Filed: Apr. 4, 2016

(65) Prior Publication Data
US 2016/0213265 A1 Jul. 28, 2016

Related U.S. Application Data

(63) Continuation of application No. 12/263,423, filed on Oct. 31, 2008, now Pat. No. 9,301,698.

(51) Int. Cl.
| | | |
|---|---|---|
| *A61B 5/021* | (2006.01) | |
| *A61B 5/0215* | (2006.01) | |
| *A61N 1/365* | (2006.01) | |
| *A61B 5/0205* | (2006.01) | |
| *A61N 1/372* | (2006.01) | |
| *A61B 5/00* | (2006.01) | |

(52) U.S. Cl.
CPC ........ *A61B 5/02055* (2013.01); *A61B 5/0215* (2013.01); *A61B 5/4836* (2013.01); *A61B 5/686* (2013.01); *A61B 5/7203* (2013.01); *A61N 1/36514* (2013.01); *A61N 1/36564* (2013.01); *A61N 1/37258* (2013.01)

(58) Field of Classification Search
CPC .............. A61N 1/3627; A61N 1/36514; A61N 1/36564; A61B 5/021
See application file for complete search history.

(56) References Cited

U.S. PATENT DOCUMENTS

| | | |
|---|---|---|
| 4,712,555 A | 12/1987 | Thornander et al. |
| 4,731,051 A | 3/1988 | Fischell |

(Continued)

FOREIGN PATENT DOCUMENTS

| | | |
|---|---|---|
| EP | 721786 B1 | 3/1998 |
| EP | 0867146 B1 | 2/2004 |

(Continued)

OTHER PUBLICATIONS (PCT/US2009/061313) PCT Notification of Transmittal of the International Search Report and the Written Opinion of the International Searching Authority.

*Primary Examiner* — William J Levicky

(57) ABSTRACT

The present disclosure provides an apparatus and method of detecting ischemia with a pressure sensor. The method can include obtaining a pressure signal and determining a pressure rate of change. The method can also include identifying at least one of impaired relaxation and impaired contractility in order to detect ischemia.

9 Claims, 11 Drawing Sheets

(56) References Cited

U.S. PATENT DOCUMENTS

| | | |
|---|---|---|
| 4,788,980 A | 12/1988 | Mann et al. |
| 4,940,052 A | 7/1990 | Mann et al. |
| 4,944,298 A | 7/1990 | Sholder |
| 4,947,845 A | 8/1990 | Davis |
| 5,113,004 A | 5/1992 | Yanagisawa et al. |
| 5,113,869 A | 5/1992 | Nappholz et al. |
| 5,135,004 A | 8/1992 | Adams et al. |
| 5,199,428 A | 4/1993 | Obel et al. |
| 5,203,326 A | 4/1993 | Collins |
| 5,313,953 A | 5/1994 | Yomtov et al. |
| 5,328,460 A | 7/1994 | Lord et al. |
| 5,466,254 A | 11/1995 | Helland |
| 5,472,453 A | 12/1995 | Alt |
| 5,476,483 A | 12/1995 | Bornzin et al. |
| 5,514,162 A | 5/1996 | Bornzin et al. |
| 5,531,768 A | 7/1996 | Alferness |
| 5,899,927 A | 5/1999 | Ecker et al. |
| 5,960,797 A | 10/1999 | Kramer et al. |
| 6,016,443 A | 1/2000 | Ekwall et al. |
| 6,021,350 A | 2/2000 | Mathson |
| 6,108,577 A | 8/2000 | Benser |
| 6,112,116 A | 8/2000 | Fischell et al. |
| 6,115,628 A | 9/2000 | Stadler et al. |
| 6,128,526 A | 10/2000 | Stadler et al. |
| 6,233,486 B1 | 5/2001 | Ekwall et al. |
| 6,249,705 B1 | 6/2001 | Snell |
| 6,256,538 B1 | 7/2001 | Ekwall |
| 6,264,606 B1 | 7/2001 | Ekwall et al. |
| 6,272,379 B1 | 8/2001 | Fischell et al. |
| 6,377,852 B1 | 4/2002 | Bornzin et al. |
| 6,381,493 B1 | 4/2002 | Stadler et al. |
| 6,438,408 B1 | 8/2002 | Mulligan et al. |
| 6,468,263 B1 | 10/2002 | Fishell et al. |
| 6,501,983 B1 | 12/2002 | Natarajan et al. |
| 6,519,493 B1 | 2/2003 | Florio et al. |
| 6,609,023 B1 | 8/2003 | Fischell et al. |
| 6,869,404 B2 | 3/2005 | Schulhauser et al. |
| 6,937,899 B2 | 8/2005 | Sheldon et al. |
| 6,985,771 B2 | 1/2006 | Fischell et al. |
| 7,082,330 B2 | 7/2006 | Stadler et al. |
| 7,096,064 B2 | 8/2006 | Deno et al. |
| 7,107,096 B2 | 9/2006 | Fischell et al. |
| 7,142,911 B2 | 11/2006 | Boileau et al. |
| 7,225,015 B1 | 5/2007 | Min et al. |
| 7,272,436 B2 | 9/2007 | Gill et al. |
| 7,277,745 B2 | 10/2007 | Natarajan et al. |
| 7,297,114 B2 | 11/2007 | Gill et al. |
| 7,572,228 B2 | 8/2009 | Wolinsky et al. |
| 8,021,307 B2 | 9/2011 | White et al. |
| 8,118,749 B2 | 2/2012 | White et al. |
| 8,265,739 B1 | 9/2012 | Boileau et al. |
| 8,353,841 B2 | 1/2013 | White et al. |
| 8,355,777 B2 | 1/2013 | White et al. |
| 9,301,698 B2 | 4/2016 | Audet et al. |
| 2002/0038091 A1 | 3/2002 | Starobin et al. |
| 2002/0143265 A1 | 10/2002 | Ackerman et al. |
| 2003/0045805 A1 | 3/2003 | Sheldon et al. |
| 2003/0158492 A1 | 8/2003 | Sheldon et al. |
| 2004/0044393 A1 | 4/2004 | Yarden et al. |
| 2004/0077962 A1 | 4/2004 | Kroll |
| 2005/0075673 A1 | 4/2005 | Warkentin et al. |
| 2007/0270934 A1 | 11/2007 | Stern et al. |
| 2008/0082135 A1 | 4/2008 | Arcot-Krishnamurthy et al. |
| 2008/0177156 A1 | 7/2008 | Zhang et al. |
| 2008/0177194 A1 | 7/2008 | Zhang et al. |
| 2008/0287602 A1 | 11/2008 | Kuhlmann et al. |
| 2008/0287818 A1 | 11/2008 | Shelchuk et al. |
| 2010/0152804 A1* | 6/2010 | Kleckner ............ A61N 1/36114 607/17 |
| 2010/0274141 A1* | 10/2010 | Patangay ............... A61B 5/024 600/485 |

FOREIGN PATENT DOCUMENTS

| | | |
|---|---|---|
| EP | 1 982 647 A3 | 10/2008 |
| WO | WO 92/16257 | 10/1992 |

\* cited by examiner

| Left Ventricular Ischemia ||||| 
|---|---|---|---|---|
| Sensor Placement | Systolic Pressure | Diastolic Pressure | Contraction dP/dt | Relaxation dP/dt |
| Left Ventricle | Decrease | Increase | Less Positive | Less Negative |
| Right Ventricle | Increase | Same | More Positive | Same |
| Pulmonary Artery | Increase | Increase | --- | --- |
| Left Atrium | Increase | Increase | --- | --- |
| Right Ventricular Ischemia ||||| 
| Sensor Placement | Systolic Pressure | Diastolic Pressure | Contraction dP/dt | Relaxation dP/dt |
| Left Ventricle | May Decrease | Decrease | May Increase | Same |
| Right Ventricle | Decrease | Increase | Less Positive | Less Negative |
| Pulmonary Artery | Decrease | Same | --- | --- |
| Left Atrium | Same | Decrease | --- | --- |
| Left and Right Ventricular Ischemia ||||| 
| Sensor Placement | Systolic Pressure | Diastolic Pressure | Contraction dP/dt | Relaxation dP/dt |
| Left Ventricle | Decrease | Increase | Less Positive | Less Negative |
| Right Ventricle | Decrease | Increase | Less Positive | Less Negative |
| Pulmonary Artery | Decrease | Increase | --- | --- |
| Left Atrium | Decrease | Increase | --- | --- |

FIGURE 8

METHOD AND APPARATUS TO DETECT ISCHEMIA WITH A PRESSURE SENSOR

RELATED APPLICATION

This application is a continuation of U.S. patent application Ser. No. 12/263,423 (now allowed), filed Oct. 31, 2008 entitled "METHOD AND APPARATUS TO DETECT ISCHEMIA WITH A PRESSURE SENSOR", which is herein incorporated by reference in its entirety.

TECHNICAL FIELD

This disclosure relates generally to a method and apparatus to detect ischemia with a pressure sensor.

BACKGROUND

The heart consists of two pumps. The right heart pumps blood through the lungs to the left heart which pumps the blood out to the rest of the body. The right and left ventricles are the pumping chambers for each side of the heart. The cardiac cycle is separated into two periods, systole and diastole.

Systole is the period in which the ventricles contract and eject blood into the aorta (left side) and the pulmonary artery (right side). As systole begins, an electrical signal spreads across the ventricles causing depolarization of the cardiac muscle cells. During depolarization, ions (sodium, potassium, and calcium) move into and out of the muscle cell. The right and left ventricles begin to contract and the blood pressure in each chamber begins to rise. When the pressure in each ventricle surpasses the pressure in its respective atrium, the valve between that ventricle and atrium closes, beginning the period of isovolumic contraction. The sudden stop of the movement of blood and the tensing of the ventricle around the incompressible blood results in the first heart sound (S1). During isovolumic contraction, the ventricular muscles continue to contract, causing the pressure in the blood to rise rapidly until it surpasses the pressure of the blood in the aorta or the pulmonary artery. At this point, the aortic and pulmonary valves open and blood is ejected. Pressure continues to build in the ventricles during the ejection phase until a point where the muscles stop contracting and begin to relax. This point marks the peak systolic pressure. In order for the cardiac muscle to relax, the cardiac muscle cells must repolarize with movement of ions through the cell membrane. As the muscles begin to relax, the pressures in the ventricles begin to fall until they drop below the pressures in the aorta and the pulmonary artery, causing the aortic and pulmonary valves to close. This ends systole and is marked by the generation of the second heart sound (S2).

Diastole begins with the isovolumic relaxation phase, during which all valves are shut. As the ventricles continue to relax, the pressures in the ventricles drop below the pressures in their respective atria. At this point, the mitral and tricuspid valves open and blood passively flows into the ventricles. During the passive filling phase, blood from the atria flows into and begins filling the ventricles. At the start of the passive filling phase, the ventricles are still relaxing and the pressures continue to drop, even though blood is beginning to fill the ventricle. Eventually, the blood pressure in the atrium and the ventricle become nearly equal and the blood pressure stops dropping. This is called ventricular diastolic pressure and is associated with the atrial filling pressure. Finally, the atria receive a signal to contract and a final bolus of blood is pushed into the ventricle before systole begins.

Ischemia is a leading cause of mortality and involves oxygen starvation of the myocardium. Once severe ischemia begins, it is critical that appropriate therapy begin within one to two hours in order to prevent severe damage to the heart muscle. Unfortunately, many episodes of myocardial ischemia do not cause excessive pain or other noticeable warning signs, and often go undetected. If left untreated, myocardial ischemia can lead to the symptoms associated with acute coronary syndrome and the eventual cell death associated with acute myocardial infarction. Acute coronary syndrome generally includes the clinical symptoms associated with unstable angina, non-ST segment elevation or non-Q-wave myocardial infarction, and ST segment elevation or Q-wave myocardial infarction. Early detection of myocardial ischemia provides the opportunity for a wide range of effective therapies such as surgical revascularization, neural stimulation, and drug delivery to reduce cardiac workload or improve cardiac circulation.

An electrocardiogram (ECG) or electrogram (EGM) presents a PQRST waveform sequence that characterizes the cyclical cardiac activity of a patient. The T-wave can be used to identify an ischemic condition. The ST segment, also associated with the repolarization of the ventricles, is typically close in amplitude to the baseline (i.e., isoelectric amplitude) of the signal sensed between consecutive PQRST sequences. During episodes of myocardial ischemia in the left ventricle, the ST segment amplitude deviates from the baseline. Accordingly, deviation in the ST segment is often used to identify an occurrence of myocardial ischemia.

Unfortunately, the use of the ST segment as an indicator of ischemia can be unreliable. The ST segment may deviate from the baseline due to other factors, causing false indications of myocardial ischemia. For example, the ST segment may deviate from the baseline due to changes in the overall PQRST complex, possibly caused by axis shifts, electrical noise, cardiac pacing stimuli, drugs, and high sinus or tachycardia rates that distort the PQRST complex. Consequently, the reliability of the ST segment as an indicator of myocardial ischemia can be uncertain.

In addition to the electrical activity of the heart, the mechanical activity of the heart (e.g., heart contractility), is affected during ischemic episodes. The term "contractility" generally refers to the ability of the heart to contract, and may indicate a degree of contraction. The dynamic mechanical activity of the heart can be represented by a heart acceleration signal or a pressure signal in order to provide an indication of heart contractility.

When a patient is experiencing chest pain or other sever symptoms, he or she eventually arrives at the emergency room after some amount of time. When the patient arrives at the emergency room, a twelve-lead ECG is used to measure the electrical activity of the heart. However, even a twelve-lead ECG has only about fifty percent sensitivity to acute myocardial infarction in the emergency room. When the patient arrives at the emergency room, cardiac biomarkers are also often measured. Cardiac biomarkers are substances that are released into the blood when the heart is damaged (e.g., troponin). The best biomarkers are chosen because the normal background concentration is near zero (i.e., anything above zero is abnormal), which leaves little room for error. Increases in cardiac biomarkers can identify patients with acute coronary syndrome, allowing an accurate diagnosis leading to appropriate treatment of their condition. Unfortunately, the biomarkers are released only once the muscle cells being to die and it can take about four to six hours for the biomarker concentrations to reach critical levels. By this time, however, many heart muscle cells would have died and the heart muscle would be severely damaged.

The symptoms of acute coronary syndrome include chest pain, pressure, nausea, and/or shortness of breath. These symptoms are associated with heart attacks and angina, but they may also be seen with non-heart-related conditions. In addition, these symptoms may be misinterpreted by the patient, leading to long delays before reaching the emergency department.

Heart sound monitors have also been proposed to detect ischemia. These heart sound monitors attempt to detect the S4 heart sound that is produced just after atrial contraction at the end of diastole by the sound of blood being forced into a stiff/hypertrophic ventricle. The S4 heart sound is a sign of a pathologic state, such as a failing left ventricle. However, the S4 heart sound is small and difficult to hear and its appearance does not always correlate to ischemia. Some people normally have the S4 heart sound while not experiencing ischemia.

SUMMARY

In one or more embodiments, a method is provided for detecting ischemia with a pressure sensor. The method includes obtaining a pressure signal and determining a pressure rate of change based on the pressure signal. The method also includes identifying impaired relaxation and/or impaired contractility based on the pressure rate of change in order to detect ischemia.

In one or more embodiments, an implantable medical device (IMD) is provided including a data collection module configured to obtain a pressure signal and a data processing module coupled to the data collection module. The data processing module is configured to determine a pressure rate of change based on the pressure signal. The data processing module is configured to identify impaired relaxation and/or impaired contractility based on the pressure rate of change in order to detect ischemia. The IMD can include a therapy module coupled to the data processing module. The therapy module can be configured to deliver therapy and/or generate an alert when impaired relaxation and/or impaired contractility are identified.

DRAWINGS

The above-mentioned features and objects of the present disclosure will become more apparent with reference to the following description taken in conjunction with the accompanying drawings wherein like reference numerals denote like elements and in which.

Figure 6:
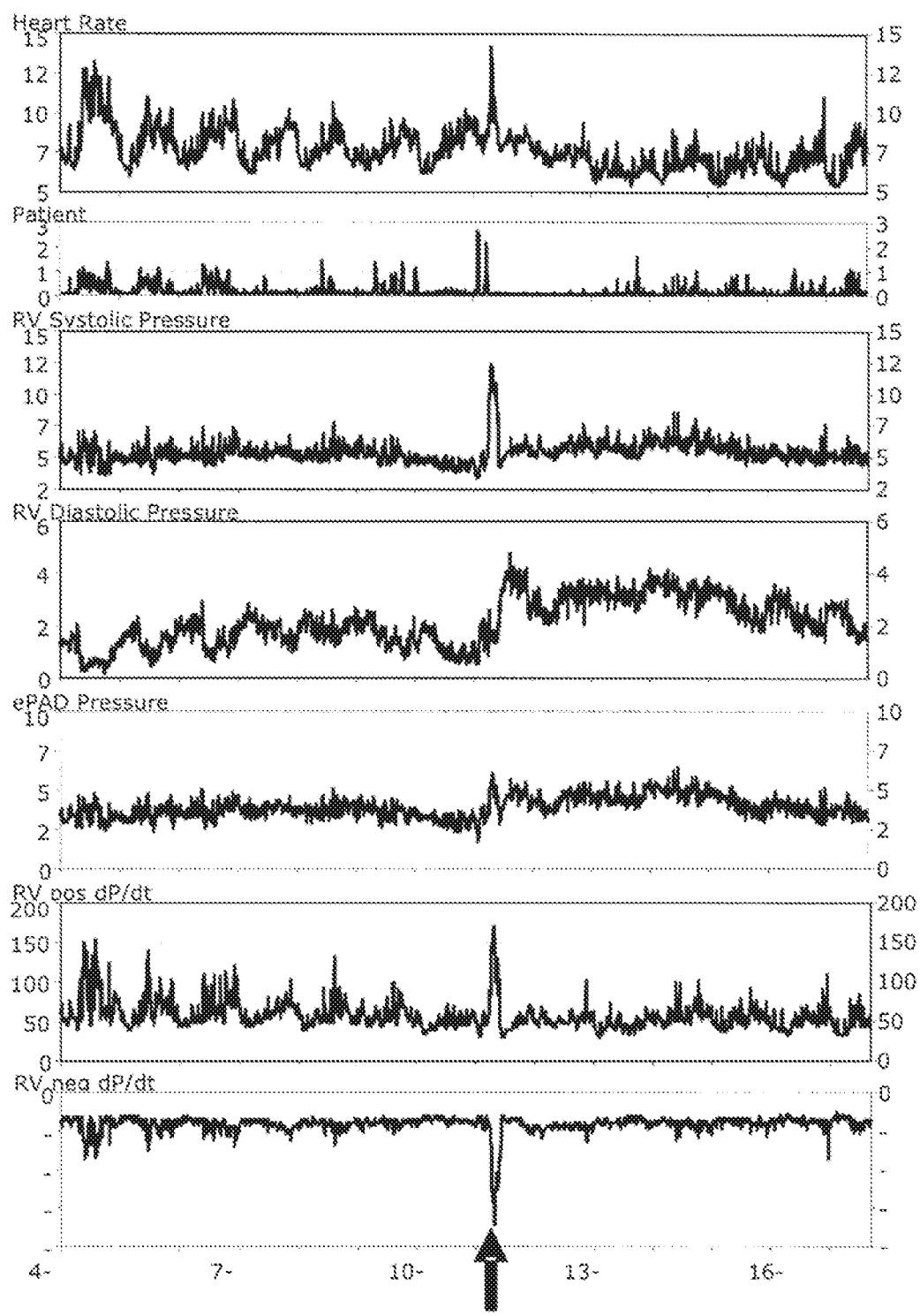

FIG. 6 includes examples of repeated measured values for heart rate, patient activity, right ventricular systolic pressure, right ventricular diastolic pressure, pulmonary artery pressure, and the positive or negative rates of change of right ventricular pressure before, during, and after an acute left ventricular ischemic event.

Figure 7:
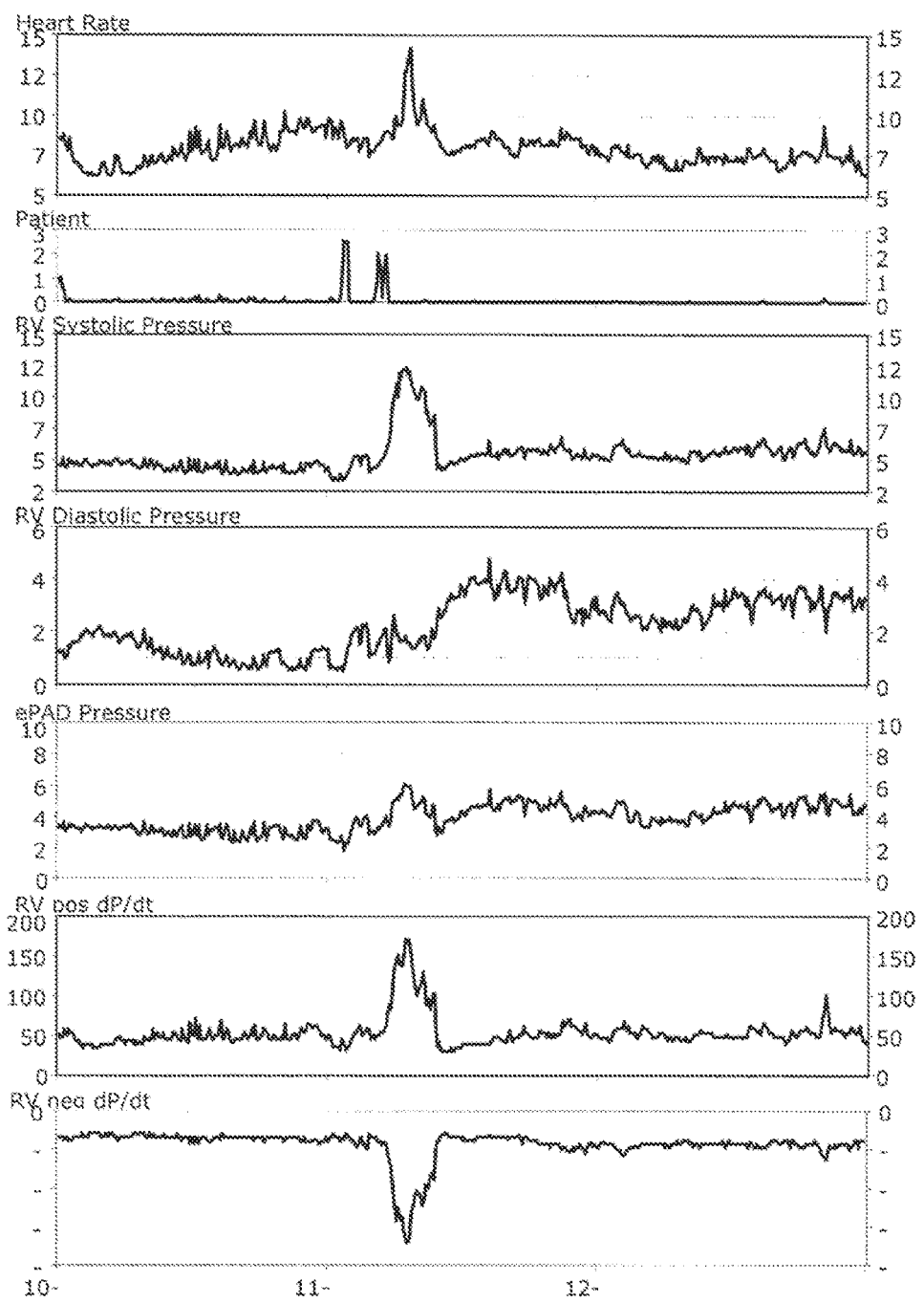

FIG. 7 includes portions of the measured values of FIG. 6 corresponding to a time period of detected left ventricular ischemia.

FIG. 8 is a chart from which detection algorithms can be established.

Figure 9:
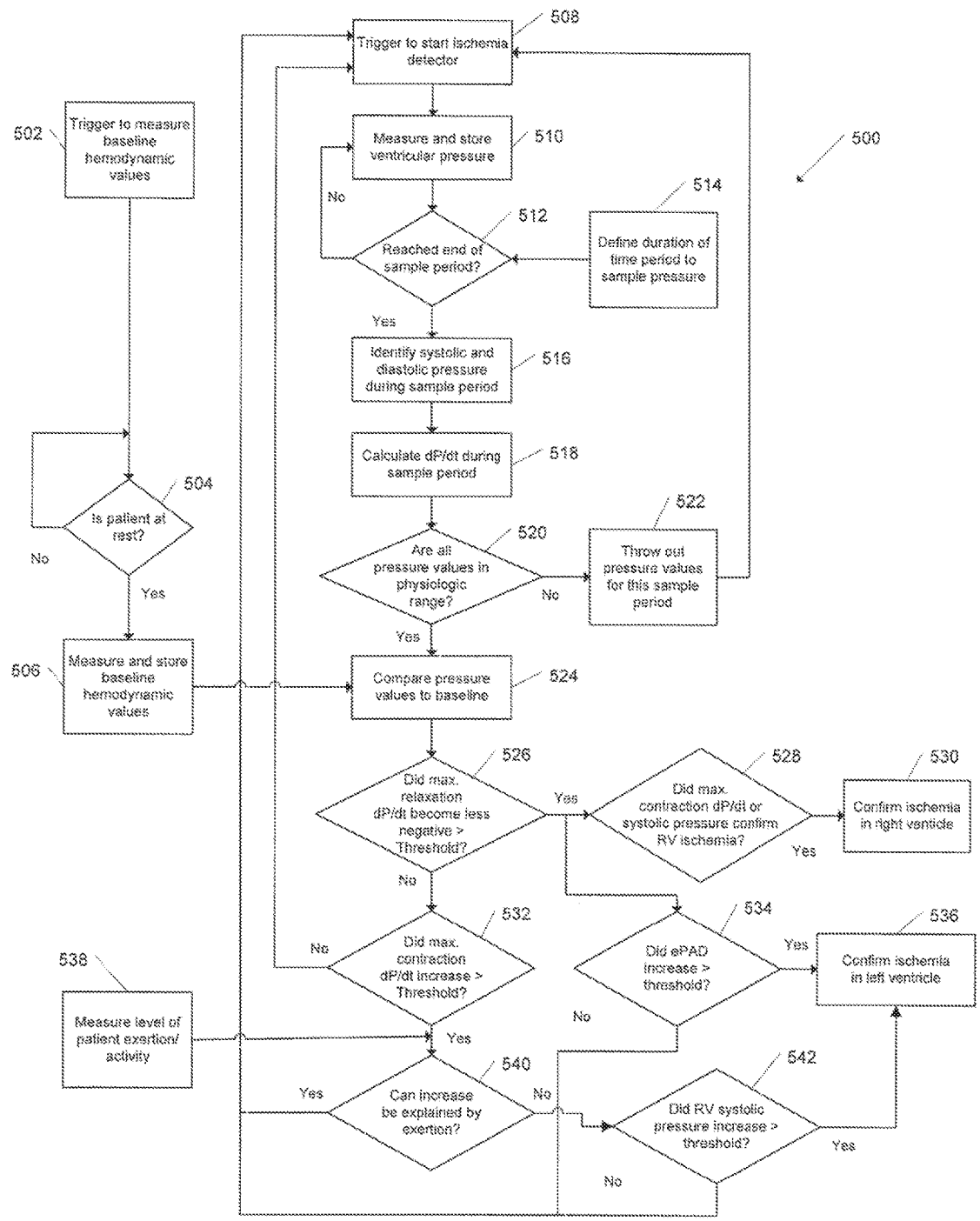

FIG. 9 is a flow chart of a method in accordance with one embodiment of the present disclosure.

Figure 10:
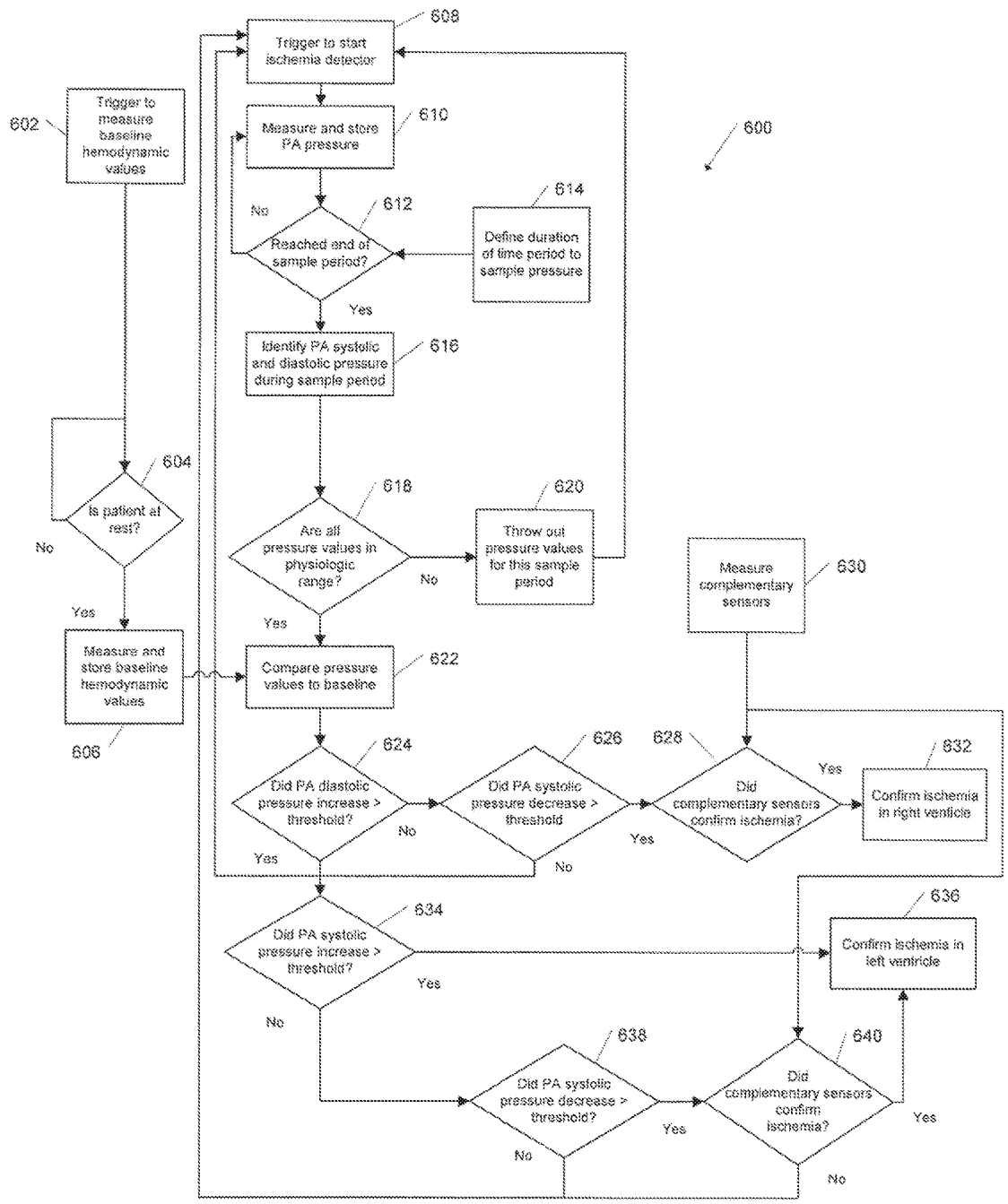

FIG. 10 is a flow chart of a method in accordance with one embodiment of the present disclosure.

Figure 11:
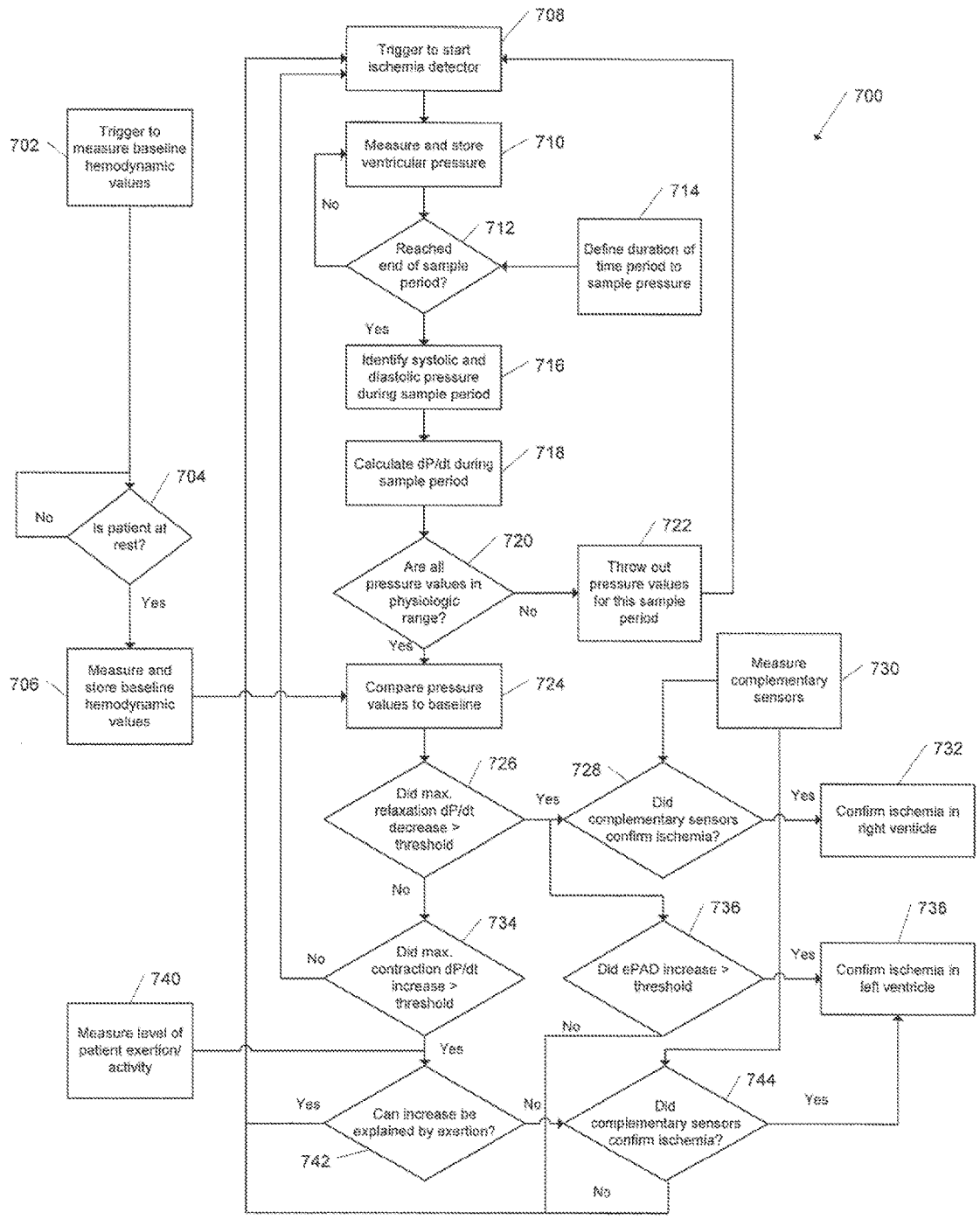

FIG. 11 is a flow chart of a method in accordance with one embodiment of the present disclosure.

DETAILED DESCRIPTION

The present disclosure describes a method and apparatus to detect ischemia with a pressure sensor. Some embodiments of the present disclosure can be used in conjunction with an implantable medical device (IMD).

The following detailed description is merely illustrative only and is not intended to limit the application and uses of the present disclosure. Furthermore, there is no intention to be bound by any expressed or implied theory presented in the preceding technical field, background, brief summary or the following detailed description.

The invention may be described herein in terms of functional and/or logical block components and various processing steps. It should be appreciated that such block components may be realized by any number of hardware, software, and/or firmware components configured to perform the specified functions. For example, an embodiment may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that the present disclosure may be practiced in conjunction with any number of medical devices and therapies and that the system described herein is merely one exemplary application.

For the sake of brevity, conventional techniques related to IMD sensor signal processing, pressure sensing, the adjustment and control of IMD therapy signals, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

Figure 4:
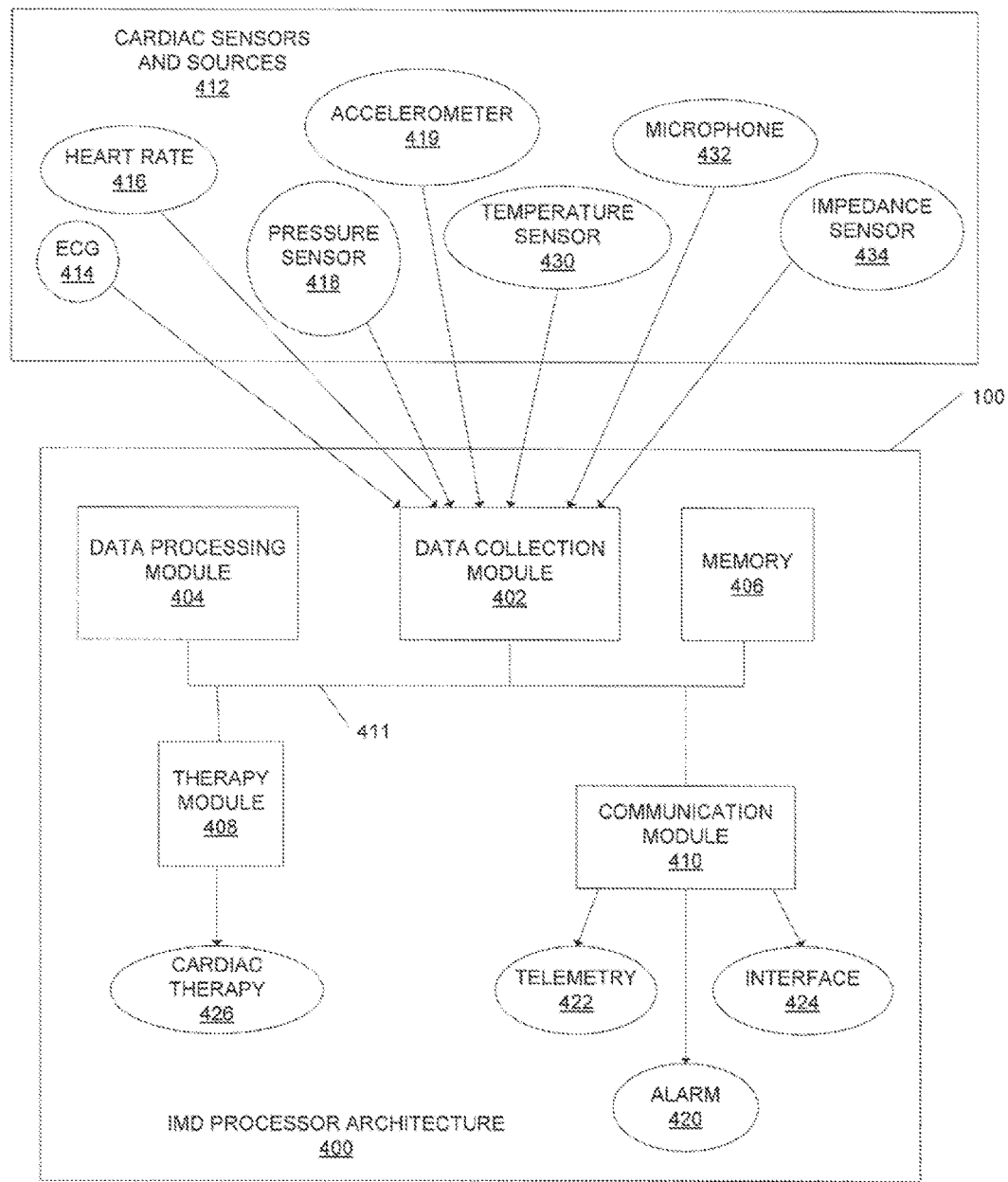
FIG. 4 is a schematic representation of a portion of an IMD configured in accordance with an embodiment of the present disclosure.

The following description refers to elements or features being "connected" or "coupled" together. As used herein, unless expressly stated otherwise, "connected" means that one element/feature is directly, indirectly, or wirelessly connected to another element/feature, and not necessarily mechanically. Likewise, unless expressly stated otherwise, "coupled" means that one element/feature is directly or indirectly coupled to another element/feature, and not necessarily mechanically. Thus, although the schematic shown in FIG. 4 depicts one example arrangement of processing elements, additional intervening elements, devices, features, or components may be present in an actual embodiment (assuming that the functionality of the system is not adversely affected).

In connection with the operation of an IMD, implantable sensors may be expected to provide diagnostic data to the IMD and/or to facilitate automated feedback control of the IMD. For example, direct measurement of pressure may be well suited to detect cardiac events. It would also be useful, however, if the same implantable pressure sensor could be used to optimize device timing. In this regard, an example embodiment incorporates real-time pressure signals for use as feedback control (preferably closed loop, but also applicable to open loop) of IMD settings or operational parameters.

There are a number of physiologic conditions that affect the pressures generated by the ventricles. Some of the conditions that may increase the rate at which the ventricle can generate pressure during systole (dP/dt) are an increase in exertion or stress, the release of catecholamines into the blood system, the activation of the autonomic nervous system, an increase in the amount of blood in the chamber prior to the start of systole. This last condition is known as the Frank-Starling effect in which an increase in the distention (filling) of the ventricle results in a stronger contraction. The higher filling can result either from a delay in the start of systole or from an increase in the filling pressure.

Figure 5:
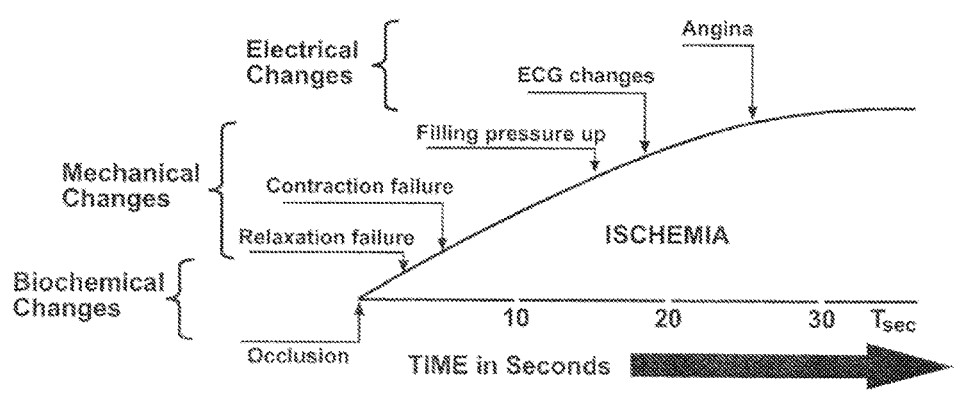
FIG. 5 is a schematic representation of the changes in the mechanical and electrical activity of the heart as the severity of ischemia increases with time.

As shown in FIG. 5, ischemia in a ventricle has a number of effects as the depth of ischemia increases. One of the first effects is that the ability of the heart muscle to relax is impaired. This is a result of an inability to adequately repolarize the cells after a contraction. The "stiffening" of the ventricle means that the blood pressure within an ischemic ventricle will not decrease as fast as in an adequately perfused ventricle. Therefore, the dP/dt during relaxation will be less negative during ischemia.

Next, the ability of the ischemic ventricle to generate contractile force will be impaired. Therefore, during contraction, the blood pressure within an ischemic ventricle will not increase as fast as in an adequately perfused ventricle. Therefore, the dP/dt during contraction will be less positive during ischemia. This will also result in a decrease in the maximum systolic pressure from the affected ventricle.

The body has a number of compensatory mechanisms that can be activated when conditions change. In the case when ischemia in the left ventricle causes a decrease in the LV systolic pressure, this will result in a decrease in the arterial systolic pressure. Baroreceptors in the neck note the change and send signals to activate the autonomic nervous system to cause an increase in the contractile force of the ventricles. Because of the ischemia, the left ventricle may not be able to respond significantly to the signal. The non-ischemic right side, however, will see a significant increase in its maximum dP/dt during contraction and will reach a higher RV systolic pressure. The increase in right sided pressure, coupled with the stiffening of the left ventricle, will increase the left side filling pressure and can be measured as an increase in left atrial pressure and left ventricular diastolic pressure. This increase in filling pressure will have some positive effect on contractile force of the left ventricle as the unaffected LV muscle cells respond to the increase in distention (Frank-Starling).

Ischemia in the right ventricle will also affect the pressure. As with the left ventricle, the contraction would have a lower RV dP/dt and reach a lower RV systolic pressure. There would also be a less negative RV dP/dt during relaxation. The resulting decrease in the LV filling pressure would initially cause the LV to contract less vigorously (lower dP/dt) and reach a lower LV systolic pressure. The RV diastolic pressure would rise.

From the above discussion, a pressure sensor can be used to detect the presence of ischemia using changes from a baseline for the diastolic pressure, the systolic pressure, and dP/dt. This detection is dependent on which chamber is affected and where the pressure sensor is implanted.

As also shown in FIG. 5, within seconds of a coronary occlusion, a cascade of events occurs beginning with metabolic and biochemical changes in cardiac myocytes including disturbed sodium and potassium concentrations inside and outside the cells that lead to impaired ventricular relaxation and contraction. Dysfunction in relaxation and contraction lead to mechanical changes in the heart, including a rise in filling pressure to compensate for the reduced systolic pressure. Following the mechanical performance changes, changes in electrical activity can be detected in the electrocardiogram, including ST segment deviations.

In some embodiments, the present disclosure provides an IMD with an implanted pressure sensor that detects a change in filling pressure from the right or left side of the heart. The pressure sensor can be placed in the right ventricle, pulmonary artery, left atrium, or left ventricle. The pressure sensor can be a pressure sensing lead or a lead-less pressure sensor that obtains a primary pressure signal. A baseline waveform can be taken periodically when the patient is at rest. The systolic pressure, diastolic pressure, and changes in pressure with time, dP/dt, can be calculated. The dP/dt signal can be compared to the stored baseline waveform or an external baseline and can identify aberrations from the stored baseline waveform or the external baseline.

One or more complimentary sensors can be used to obtain complimentary signals that can be evaluated along with the primary pressure signal. The complimentary signals can include one or more of the following: heart rate, heart rate variability, number of premature ventricular contractions (PVC's), non-sustained ventricular tachycardia (NSVT), sustained ventricular tachycardia (SVT), time of day, electrocardiogram (ECG), patient activity, core body temperature, intra-cardiac impedance, intra-thoracic impedance, respiration rate, mixed venous oxygen saturation, wall contractility, wall tension, heart sounds, pulse oximeter, and pulse pressure. Baselines for these complimentary signals can also be stored for later comparison to current signals. In addition, the patient can have a remote control that can be activated when symptoms of ischemia are perceived. The dP/dt signal can be analyzed in combination with the complimentary signals to detect acute cardiac events. Along with the primary pressure signal, the complimentary signals can be analyzed to establish a correlation between the complimentary signals and normal hemodynamic response and to identify aberrations from the normal hemodynamic response.

In some embodiments, a baseline pressure signal can be periodically or continually compared to the primary pressure signal. The baseline pressure signal can be a stored baseline waveform from the primary pressure signal or the baseline pressure waveform can be obtained from a second pressure sensor in a different location.

In some embodiments, the primary pressure signal can be analyzed in combination with one or more of the complimentary signals. The dP/dt signal can also be evaluated for an early indication of relaxation or contraction changes. This evaluation can be used to determine the need for a further evaluation of the primary pressure signal. The pressure signal and/or the dP/dt signal can also be correlated with the patient's electrocardiogram. This combination of mechanical waveform signals and electrical waveform signals can be used to detect relaxation changes and contractility changes in the patient's heart during an acute cardiac event.

In some embodiments, the present disclosure provides a method to determine the onset of ischemia. In one embodiment, the method can include obtaining a number of complimentary signals. In addition to the primary pressure signal, the complimentary signals can be electrical, such as ST segment elevation, heart rate, heart rate variability, and/or an increasing number of PVC's. The method can also include receiving a complimentary signal from a patient activator that signals the onset of symptoms, such as chest pain. These complimentary signals can be combined with the primary pressure signal. The complimentary signals can each be given a different weight in the detection of ischemia.

FIGS. 6 and 7 illustrate the changes in the measured values for a number of variables over a 14-day period during which ischemia occurred in the left ventricle and the patient was admitted to the hospital and given thrombolitics. The traces show a relatively rapid change in heart rate, patient activity, right ventricular systolic pressure, right ventricular diastolic pressure, estimated end-diastolic pulmonary artery pressure (ePAD), and right ventricular pressure rate of change (RV dP/dt). Rapid changes in the diastolic pressure or dP/dt can indicate a rapid change in the sympathetic response, in the absence of other reasons (such as exercise), that result in ischemia.

Figure 1:
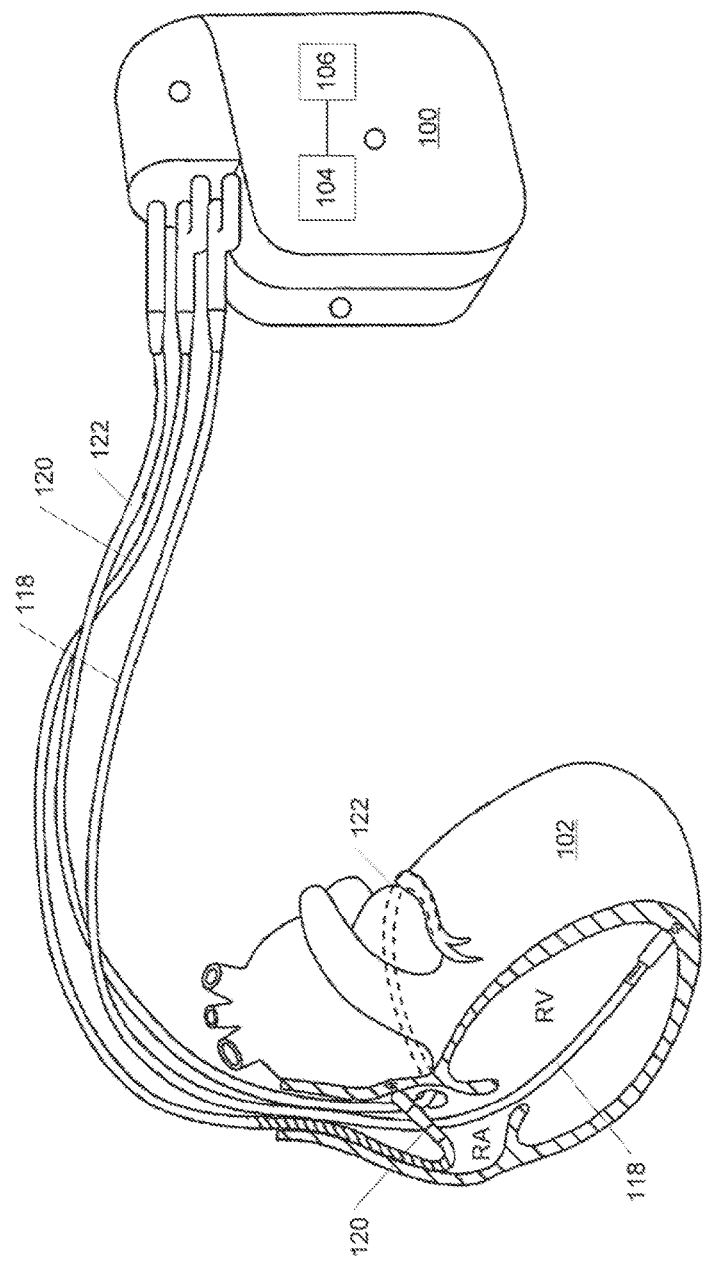
FIG. 1 is a schematic diagram of an implantable medical device (IMD) in accordance with an embodiment of the present disclosure.

FIG. 1 is an illustration of an exemplary implantable medical device (IMD) 100 connected to monitor a patient's heart 102. IMD 100 may be configured to integrate both monitoring and therapy features, as will be described below. IMD 100 collects and processes data about heart 102 from one or more sensors including a pressure sensor and an electrode pair for sensing cardiac electrogram (EGM) signals. IMD 100 may further provide therapy or other response to the patient as appropriate. As shown in FIG. 1, IMD 100 may be generally flat and thin to permit subcutaneous implantation within a human body, e.g., within upper thoracic regions or the lower abdominal region. IMD 100 is provided with a hermetically-sealed housing that encloses a processor 104, a digital memory 106, and other components as appropriate to produce the desired functionalities of the device. In various embodiments, IMD 100 is implemented as any implanted medical device capable of measuring the heart rate of a patient and a ventricular or arterial pressure signal, including, but not limited to a pacemaker, defibrillator, electrocardiogram monitor, blood pressure monitor, drug pump, insulin monitor, or neurostimulator. In some embodiments, the IMD 100 can be a pacemaker system including a hemodynamic sensor together with memory function and software download capability for optimization algorithms. A suitable IMD that may be used in various exemplary embodiments can include a mechanical sensor capable of detecting a pressure signal from inside the right ventricle of the heart. In a further embodiment, IMD 100 is any device that is capable of sensing a pressure signal and providing pacing and/or defibrillation or other electrical stimulation therapies to the heart. Another example of an IMD capable of sensing pressure-related parameters is described in commonly assigned U.S. Pat. No. 6,438,408 issued to Mulligan et al. on Aug. 20, 2002.

Processor 104 may be implemented with any type of microprocessor, digital signal processor, application specific integrated circuit (ASIC), field programmable gate array (FPGA) or other integrated or discrete logic circuitry programmed or otherwise configured to provide functionality as described herein. Processor 104 executes instructions stored in digital memory 106 to provide functionality as described below. Instructions provided to processor 104 may be executed in any manner, using any data structures, architecture, programming language and/or other techniques. Digital memory 106 is any storage medium capable of maintaining digital data and instructions provided to processor 104 such as a static or dynamic random access memory (RAM), or any other electronic, magnetic, optical or other storage medium.

As further shown in FIG. 1, IMD 100 may receive one or more cardiac leads for connection to circuitry enclosed within the housing. In the example of FIG. 1, IMD 100 receives a right ventricular endocardial lead 118, a left ventricular coronary sinus lead 122, and a right atrial endocardial lead 120, although the particular cardiac leads used will vary from embodiment to embodiment. In addition, the housing of IMD 100 may function as an electrode, along with other electrodes that may be provided at various locations on the housing of IMD 100. In alternate embodiments, other data inputs, leads, electrodes and the like may be provided. Ventricular leads 118 and 122 may include, for example, pacing electrodes and defibrillation coil electrodes (not shown) in the event IMD 100 is configured to provide pacing, cardioversion and/or defibrillation. In addition, ventricular leads 118 and 122 may deliver pacing stimuli in a coordinated fashion to provide biventricular pacing, cardiac resynchronization, extra systolic stimulation therapy or other therapies.

IMD 100 suitably collects and processes data about heart 102 from one or more sources (e.g., pressure sensor, heart rate monitor, blood pressure monitor, ECG waveform, EGM waveform, etc.). IMD 100 can obtain pressure data input from a pressure sensor that is carried by a lead, such as right ventricular endocardial lead 118, or from a lead-less pressure sensor. The right ventricular lead 118 can provide a real-time pressure signal to IMD 100 from the right ventricle of heart 120. The pressure sensor may be contained on an independent lead, or may be integrated into a pacing or defibrillation lead. In another embodiment, the pressure sensor can be contained in a module (not shown) that is physically separated from the IMD 100 but which can communicate wirelessly to the IMD 100. In alternate embodiments, other data inputs, leads, electrodes and the like may be provided. The right ventricular lead 118 may include, for example, pacing electrodes and defibrillation coil electrodes (not shown) for purposes of pacing, cardioversion, and/or defibrillation. IMD 100 may also obtain input data from other internal or external sources (e.g., as shown in FIG. 4) such as an oxygen sensor, pH monitor, accelerometer or the like.

In operation, IMD 100 obtains data about the heart 102 via the leads 118, 120, 122, and/or other sources. This data is provided to processor 104, which suitably analyzes the data, stores appropriate data in memory 106, and/or provides a response or report as appropriate. In particular, IMD 100 generates one or more therapy signals that are preferably optimized in accordance with the obtained data. In the example embodiment, IMD 100 detects an acute cardiac event and delivers an appropriate therapy or generates an alert.

Any identified cardiac episodes (e.g. an arrhythmia or heart failure decompensation) can be treated by intervention of a physician or in an automated manner. In various embodiments, IMD 100 activates an alarm upon detection of a cardiac event. Alternatively or in addition to alarm activation, IMD 100 selects or adjusts a therapy and coordinates the delivery of the therapy by IMD 100 or another appropriate device. Optional therapies that may be applied in various embodiments may include drug delivery or electrical stimulation therapies such as cardiac pacing, cardiac resynchronization therapy, extra systolic stimulation, and neurostimulation.

Figure 2:
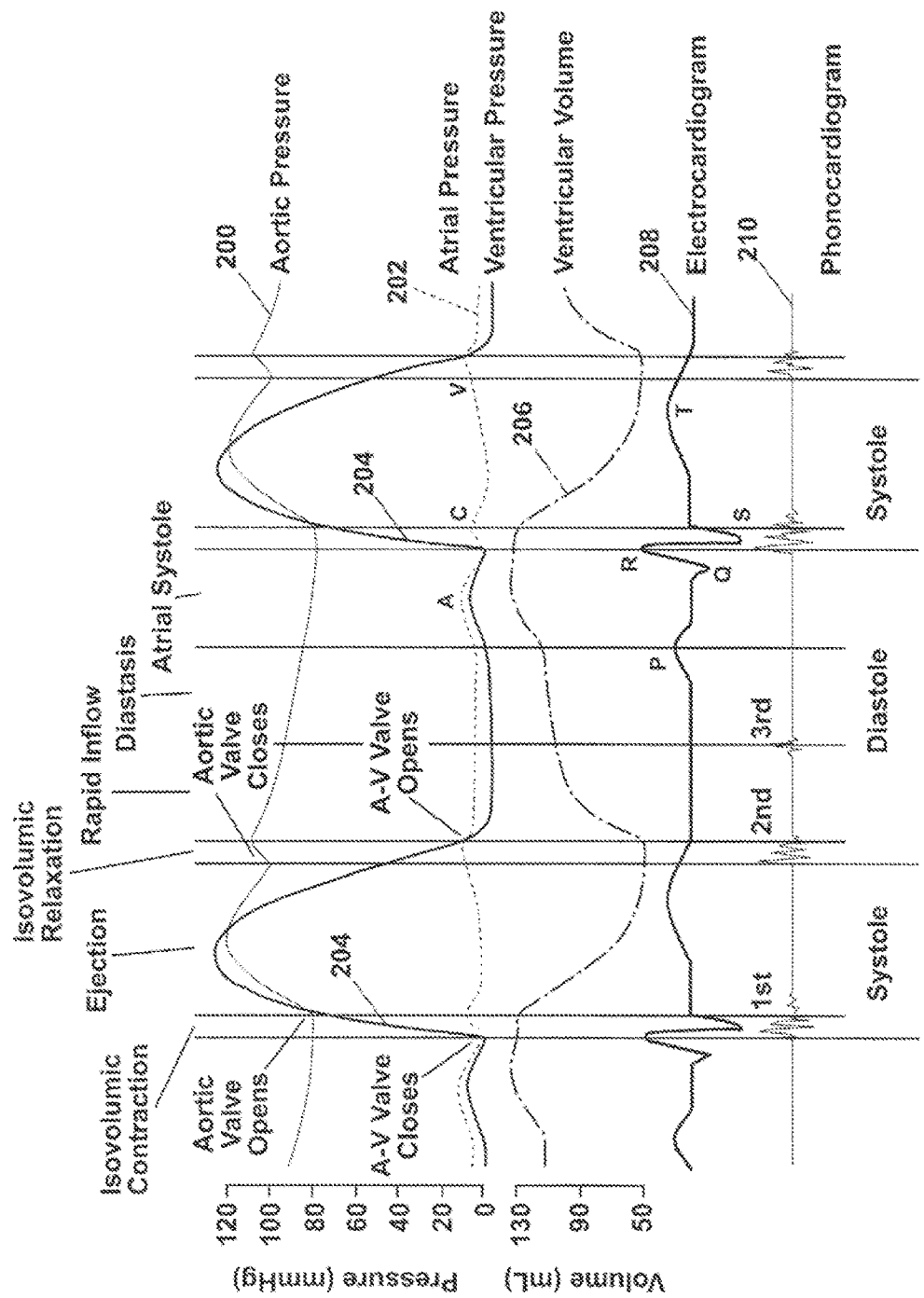
FIG. 2 is a diagram of pressures, volumes, electrical activity, and heart sounds for two cardiac cycles.

FIG. 2 is a diagram illustrating changes in aortic pressure 200, atrial pressure 202, ventricular pressure 204, and ventricular volume 206 as related in time to an electrocardiogram 208 and a phonocardiogram 210 for two cardiac cycles. Each cardiac cycle is divided into diastole, which represents ventricular filling, and systole, which represents contraction and ejection of blood from the ventricles. In some embodiments, RVDP can be measured by right ventricular lead 118. However, other pressures can be measured, such as left ventricular pressure, pulmonary artery pressure, and/or left atrial pressure.

Figure 3:
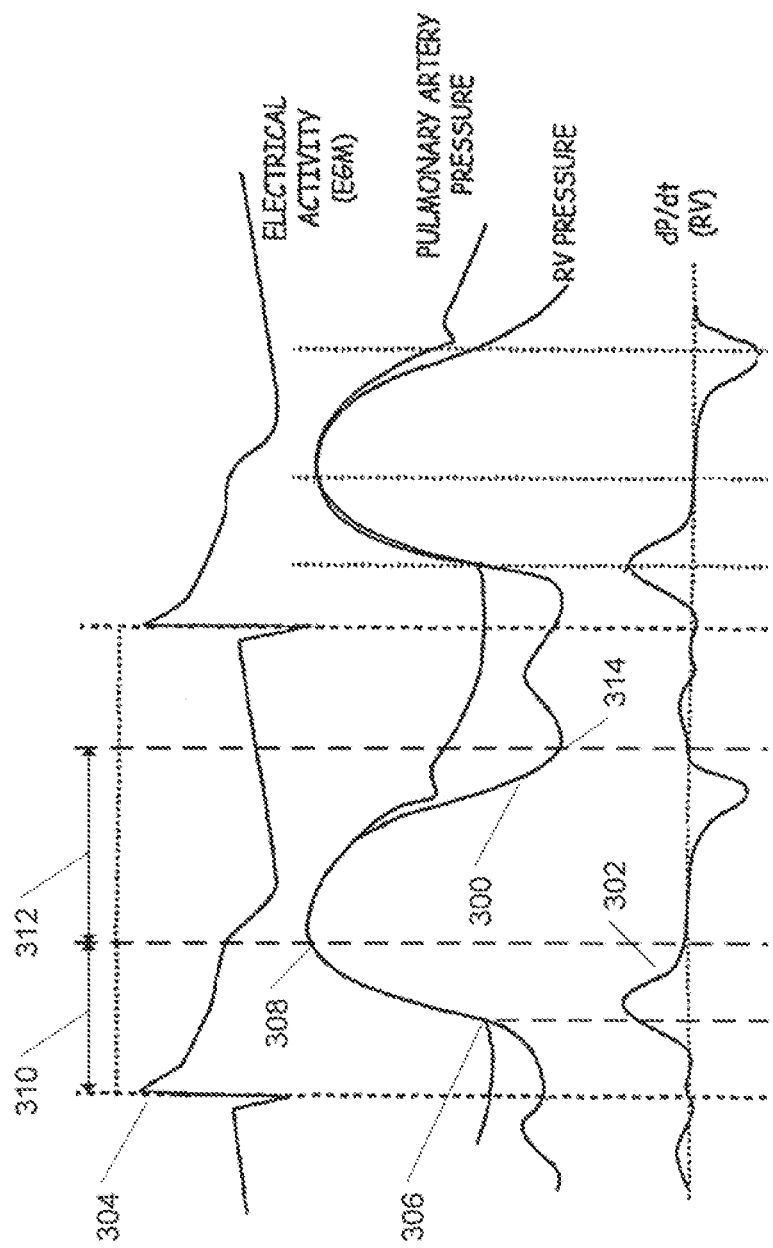
FIG. 3 is a diagram of the pressure measured in the right ventricle (RV), the pulmonary artery, and the rate of change of the pressure signal in the RV (RV dP/dt) for two cardiac cycles.

FIG. 3 is a diagram showing an example graph of a pressure signal 300 along with an example graph of a secondary signal 302 that represents the rate of change (i.e., the first derivative) of the pressure signal (i.e., the RV dP/dt signal). On the diagram, the R wave 304 of the ECG is noted, along with the periods of contraction 310 and relaxation 312 of the right ventricle. The period of contraction 310 is indicated as the rise in pressure. Contraction 310 ends when the RV pressure reaches its maximum value, which is the systolic pressure 308. During contraction 310, the dP/dt has a positive value. Also noted on the waveform is the estimated Pulmonary Diastolic Pressure (ePAD) 306. ePAD 306 is defined as the RV pressure at the time that the RV dP/dt reaches its maximum value. This pressure is closely linked to the time when the RV pressure surpasses the PA pressure and the PA valve opens. After systole is reached, the ventricle begins to relax. During this period, the dP/dt is negative. This period ends when the RV pressure reaches its minimum before the atrium contracts. This value is known as the RV diastolic pressure 314. It should be appreciated that these graphs are merely examples and that the actual pressure characteristics will vary from patient to patient, vary according to the current patient condition, and vary over time.

FIG. 4 is a schematic representation of a portion of an IMD 100 configured in accordance with an example embodiment of the present disclosure. In particular, FIG. 4 depicts an exemplary data processing layout for an IMD processor architecture 400, which may be located within the housing of a suitable IMD as described herein. In this example, processor architecture 400 includes at least a data collection module 402, a data processing module 404, a suitable amount of memory 406, a therapy module 408, and/or a communication module 410. These modules may be coupled to each other via a suitable data communication bus or arrangement 411. Each of the various modules may be implemented with computer-executable instructions stored in memory 406 and executing on processor architecture 400, or in any other practical manner. The exemplary modules and blocks shown in FIG. 4 are intended to illustrate one logical model for implementing an IMD in accordance with the invention, and should not be construed as limiting. Indeed, the various practical embodiments may have widely varying software modules, data structures, applications, processes and the like. As such, the various functions of each module may in practice be combined, augmented, optimized or otherwise differently-organized in any fashion.

In accordance with the practices of persons skilled in the art of computer programming, the present disclosure may be described herein with reference to symbolic representations of operations that may be performed by the various computing components, modules, or devices. Such operations are sometimes referred to as being computer-executed, computerized, software-implemented, or computer-implemented. It will be appreciated that operations that are symbolically represented include the manipulation by the various microprocessor devices of electrical signals representing data bits at memory locations in the system memory, as well as other processing of signals. The memory locations where data bits are maintained are physical locations that have particular electrical, magnetic, optical, or organic properties corresponding to the data bits.

When implemented in software or firmware, various elements of the IMDs described herein are essentially the code segments or instructions that perform the various tasks. The program or code segments can be stored in a processor-readable medium or transmitted by a computer data signal embodied in a carrier wave over a transmission medium or communication path. The "processor-readable medium" or "machine-readable medium" may include any medium that can store or transfer information. Examples of the processor-readable medium include an electronic circuit, a semiconductor memory device, a ROM, a flash memory, an erasable ROM (EROM), a hard disk, a fiber optic medium, or the like. The computer data signal may include any signal that can propagate over a transmission medium such as electronic network channels, optical fibers, air, electromagnetic paths, or RF links.

Data collection module 402 suitably interacts with one or more data sources 412 to obtain data about the patient. Data sources 412 include any source of information about the patient's heart and possibly other physiologic information. In various embodiments, data sources 412 may include an ECG source 414 that provides electrical impulses or other observed signals that can be used to model the patient's ECG waveform. Other data sources 412 may include a heart rate sensor 416, a pressure sensor or monitor 418, an accelerometer 419, temperature sensor 430, a microphone 432, and an impedance sensor 434. In practice, an IMD may also utilize a sensor for determining cardiac conduction time, blood pH sensors, and/or other known data sources. The various data sources 412 may be provided alone or in any combination with each other, and may vary widely from embodiment to embodiment.

The pressure sensor 418 is suitably configured to measure the real-time pressure of the patient's heart and to provide raw pressure data to data collection module 402. In turn, data collection module 402 and/or data processing module 404 can convert the raw pressure data into a usable pressure signal and the dP/dt signal for analysis as described herein. A practical IMD can utilize any suitable pressure sensor 418, including, without limitation: pressure sensors that are mounted through the wall of the heart; pressure sensors that utilize structures of the heart as a transducer membrane; and pressure sensors that are inserted through appendages or through cardiac valves. Indeed, processor architecture 400 can be configured to accommodate the specific pressure signal format and characteristics associated with the particular pressure sensor or sensors deployed with the IMD.

The accelerometer 419 can be connected to the IMD 100 by lead wires and designed to be affixed to the endocardial or epicardial walls of the left atrium, right ventricle, or left ventricle, or in the coronary sinus or the pericardial sac in order to detect mechanical contractions of the cardiac chambers. In an exemplary implementation, the accelerometer is incorporated in the lead wires which are advanced to the heart intravenously. A right ventricular accelerometer may be affixed to the endocardial surface of the right ventricle at the septal wall, while left atrial and ventricular accelerometers may be placed in the coronary sinus and cardiac veins, respectively, to sense movement of the free walls of those chambers. In another example, the accelerometer 419 can be incorporated in a module that is attached to the epicardium of the left ventricle and communicates wirelessly with the IMD 100. The accelerometer 419 can be interfaced to the data processing module 404 by the data collection module 402.

The microphone 432 can detect heart sounds, which can be amplified and filtered. The heart sounds can be compared to a signature sound pattern to derive a control signal timed to the second or "dub" heart sound, which is related to the dicrotic notch of the aortic pressure wave. In some embodiments, the microphone 432 can be mounted in one or more pacing leads arranged in or about the heart or to be mounted in the IMD 100 for acoustically sensing heart sounds transmitted through a fluid filled lumen. The microphone can also be mounted within a separate module that is implanted within the heart, on the epicardium of the heart, in the pericardial space, or under the skin of the chest and communicates to another implanted device, such as the IMD 100.

The impedance sensor 434 can include one or more electrodes coupled by one or more conductors to the data collection module 402. In some embodiments, impedance-based measurements of cardiac parameters can be acquired by an impedance lead having plural pairs of spaced surface electrodes located within the heart chamber. The spaced apart electrodes can also be disposed along impedance leads lodged in cardiac vessels, e.g., the coronary sinus and great vein or attached to the epicardium around the heart chamber. The impedance lead can be combined with other leads, such as pacing or pressure sensor leads.

The data collection module 402 suitably receives data from each of the data sources 412 by polling each of the data sources 412, by responding to interrupts or other signals generated by the data sources 412, by receiving data at regular time intervals, or according to any other temporal scheme. In particular, the data collection module 402 is configured to obtain a pressure signal from the patient for processing. Data may be received at the data collection module 402 in digital or analog format according to any protocol. If any of the data sources 412 generate analog data, the data collection module 402 suitably translates the analog signals to digital equivalents using any form of analog-to-digital conversion scheme presently known or subsequently developed. The data collection module 402 may also convert data from protocols used by the data sources 412 to data formats acceptable to the data processing module 404, as appropriate. It should be appreciated that the pressure sensor 418, the processor architecture 400, the data collection module 402, and any corresponding logical elements, individually or in combination, are example means for obtaining a pressure signal of a patient as used herein.

The data processing module 404 is any circuit, programming routine, application or other hardware/software module that is capable of processing data received from the data collection module 402. In various embodiments, the data processing module 404 is a software application executing on processor architecture 400 to implement the processes described below. Accordingly, the data processing module 404 interprets received pressure signals 300, generates or analyzes signals based upon or derived from received pressure signals 300, and/or handles other data to adjust one or more operating parameters of the IMD 100.

In an exemplary embodiment, the data processing module 404 receives pressure signal data and/or other appropriate information from the data collection module 402 and interprets the data using conventional digital signal processing techniques. For example, the data processing module 404 may generate a dP/dt signal 302 that is based upon the first derivative of the pressure signal. In this regard, the data processing module 404, the processor architecture 400, and any corresponding logical elements, individually or in combination, are example means for generating dP/dt signals 302 based upon the pressure signal 300.

The data processing module 404 is configured to identify at least one attribute of the pressure signal 300, and/or at least one attribute of a dP/dt signal 302 based upon the pressure signal 300, and correlate the identified attributes to the hemodynamic status or cardiac performance of the patient. In this manner, the pressure signal 300 data can be utilized as a feedback control mechanism to adjust the therapy delivered by the IMD 100. It should be appreciated that the data processing module 404, the processor architecture 400, and any corresponding logical elements, individually or in combination, are example means for identifying attributes of the pressure signal 300 and/or the dP/dt signal 302.

The communication module 410 is any circuit or routine that facilitates the transfer of data, information, reports, or programming instructions between the IMD 100 and an external device, system, or person (e.g., the patient, a physician, or a caregiver). In various embodiments, communication module 410 may be configured to generate an audible or visible alarm 420, handle wireless messages via a telemetry circuit 422, or manage the transmission of other data using any suitable interface 424. In this regard, the communication module 410 may facilitate open-loop feedback control of the IMD operating parameters by transmitting pressure signals 300 or pressure signal attributes to an external processing system that responds with programming instructions to adjust the AV delay or other IMD parameters in the manner described herein. In some embodiments, the alarm 420 and/or the telemetry module 422 can be used to provide a warning feature for ischemia, an acute cardiac event, disease progression, cardiac reserve, exercise tolerance, and/or congestive cardiac failure.

The therapy module 408 is any suitable circuit, software application or other component that is configured to deliver cardiac therapy 426 to the patient. In the example embodiment, the therapy module 408 is configured to provide pacing as one form of cardiac therapy 426. In some embodiments, therapy module 408 may be alternatively or additionally configured to deliver various modes of pacing, post-extrasystolic potentiation, cardioversion, defibrillation and/or any other therapy. It should be appreciated that the therapy module 408, the cardiac therapy 426, the processor architecture 400, and any corresponding logical elements, individually or in combination, are example means for automatically the therapy signal generated by the IMD 100.

The various components and processing modules of the IMD 100 may be housed in a common housing such as that shown in FIG. 1. Alternatively, portions of the IMD 100 may be housed separately. For example, portions of the therapy module 408 could be integrated with the IMD 100 or provided in a separate housing. In this case, the therapy module 408 may interact with therapy electrodes via an electrical cable, wireless link, or the interface 424.

FIG. 8 includes a chart from which detection algorithms can be established. As shown in the chart of FIG. 8, if Contraction dP/dt becomes less positive and Relaxation dP/dt becomes less negative, then ischemia is present in the same chamber as the pressure sensor. If a pressure sensor in the RV sees the RV systolic pressure increase and/or the Contraction dP/dt increase from a baseline, then ischemia is present in the LV. This assumes that a significant increase in activity has not caused the changes. If a Pressure Sensor in the LV sees a decrease in LV diastolic pressure coupled with an increase in LV dP/dt, then ischemia may be present in the RV. One confounding but important condition is for an RV pressure sensor when there is acute ischemia in both the left and right ventricle. The right side ischemia is identified using the changes in dP/dt. This may be sufficient to issue an alarm to the patient to seek medical help. If, however, the trigger is based only on LV ischemia, the systolic and diastolic values may not be sufficient. In this case, the ePAD (estimate Pulmonary Artery Diastolic) pressure can be useful. ePAD is the value of the pressure in the right ventricle at the time of maximum contraction dP/dt and represents the pressure at which the PA valve opens at the end of isovolumic contraction. From the analysis above, the PA diastolic pressure and, therefore, the ePAD, increases at the onset of acute ischemia in the left ventricle. Similar logic can be used to identify detection algorithms for a sensor placed in the left atrium or the pulmonary artery. In particular, a sudden increase in the left atrial diastolic or PA diastolic pressure might indicate the onset of ischemia in the left ventricle. According to the chart of FIG. 8, FIGS. 9-11 illustrate processes 500, 600, 700 for cases when pressure sensors are placed in the right ventricle or the pulmonary arteries. A similar process can be performed for a pressure sensor located in the left ventricle based on the chart of FIG. 8.

FIGS. 9-11 are flow diagrams of IMD parameter control processes 500, 600, 700, which may be performed by an IMD 100 configured in accordance with an example embodiment of the present disclosure. The various tasks performed in connection with processes 500, 600, 700 may be performed by software, hardware, firmware, or any combination thereof. For illustrative purposes, the following description of processes 500, 600, 700 may refer to elements mentioned above in connection with FIGS. 1 and 4. In practical embodiments, portions of processes 500, 600, 700 may be performed by different elements of the described system, e.g., data sources 412, processor architecture 400, or any component thereof. It should be appreciated that processes 500, 600, 700 may include any number of additional or alternative tasks, the tasks shown in FIGS. 9-11 need not be performed in the illustrated order, and processes 500, 600, 700 may be incorporated into a more comprehensive procedure or process having additional functionality not described in detail herein. IMD parameter control processes 500, 600, 700 represent methods for analyzing a patient's pressure data and detecting an acute cardiac event, such as ischemia, acute coronary syndrome, and acute myocardial infarction.

As shown in FIG. 9, process 500 includes measuring pressure in the RV. Process 500 includes triggering the data collection module 402 to measure baseline hemodynamic values (task 502). The accelerometer 419 or other methods can be used to determine if the patient is at rest (task 504). If the patient is not at rest, the process 500 can wait until the patient is at rest. If the patient is at rest, the data collection module 402 can measure and store baseline hemodynamic values (task 506) (e.g., for about one hour or another suitable time period). In some embodiments, baseline waveforms can be collected with a suitable monitoring device, such as a monitoring device including a mechanical sensor capable of detecting a pressure signal from inside the right ventricle of the heart. In some embodiments, the suitable monitoring device can be used to obtain the pressure signals 300 and to extract the dP/dt signal 302, as shown in FIG. 3.

Process 500 includes triggering the start of ischemia detection (task 508), which can include a trigger signal from the ECG 414, a trigger based on a time period (e.g., about every five minutes), a trigger from the patient, a remote trigger from a physician, etc. The data collection module 402 can measure and store the ventricular pressure from the pressure sensor 418 positioned in the RV (task 510). The data processing module 404 can determine if the end of the sample period has been reached (task 512). The duration of the time period to obtain the ventricular pressure can be defined (task 514) (e.g., about two seconds, at the start of an R wave until the end of an R wave, multiple heart beats that are averaged, etc.).

When the end of the sample period has been reached, the data processing module 404 can identify the systolic and diastolic pressures (as shown in FIG. 3) during the sample period (task 516). The data processing module 404 can calculate dP/dt during the sample period (task 518). The data processing module 404 can determine whether all the pressure values are within their physiological ranges (task 520), for example, to identify noise and/or artifacts. If the values are not within their physiological ranges, the process 500 can throw out the pressure values for the sample period (task 522) and return to the start of the ischemia detection (task 508).

If the values are within their physiological ranges, the data processing module 404 can compare the pressure values to the baseline values (task 524) that were previously measured and stored (task 506). The data processing module 404 can then determine whether the maximum relaxation dP/dt value became less negative than a threshold (task 526) (e.g., about 25-50% beyond the baseline value or preferably about 33% beyond the baseline value). If yes, the data processing module 404 can determine whether the contraction dP/dt or the systolic pressure confirm RV ischemia (task 528). If yes, the process 500 can confirm ischemia in the RV (task 530). In addition, the data processing module 404 can determine whether the ePAD value increased beyond a threshold (task 534) (e.g., about 25-50% beyond the baseline value or preferably about 33% beyond the baseline value). If yes, the process 500 can also confirm ischemia in the LV (task 536).

If the maximum relaxation dP/dt did not become less negative than a threshold (task 526), the data processing module 404 can determine whether the maximum contraction dP/dt increased beyond a threshold (task 532) (e.g., about 25-50% beyond the baseline value or preferably about 33% beyond the baseline value). If no, the process 500 can return to the start of the ischemia detection (task 508). If yes, the process 500 can measure the patient's level of exertion and/or activity (task 538) (e.g., based on the heart rate 416, the accelerometer 419, the temperature sensor 430, respiration data, pressures, etc.). The data processing module 404 can then determine whether the increase can be explained by exertion (task 540). If no, the data processing module 404 can determine whether the RV systolic pressure increased beyond a threshold (task 542) (e.g., about 25-50% beyond the baseline value or preferably about 33% beyond the baseline value). If yes, the process 500 can confirm ischemia in the LV (task 536). If no, the process can return to the start of the ischemia detection (task 508).

As shown in FIG. 10, process 600 includes measuring pressure in the PA. Process 600 includes triggering the data collection module 402 to measure baseline hemodynamic values (task 602). The accelerometer 419 or other methods can be used to determine if the patient is at rest (task 604).

If the patient is not at rest, the process 600 can wait until the patient is at rest. If the patient is at rest, the data collection module 402 can measure and store baseline hemodynamic values (task 606) (e.g., for about one hour or another suitable time period). In some embodiments, baseline waveforms can be collected with a suitable monitoring device, such as a monitoring device including a mechanical sensor capable of detecting a pressure signal from inside the right ventricle of the heart. In some embodiments, the suitable monitoring device can be used to obtain the pressure signals 300 and to extract the dP/dt signal 302, as shown in FIG. 3.

Process 600 includes triggering the start of ischemia detection (task 608), which can include a trigger signal from the ECG 414, a trigger based on a time period (e.g., about every five minutes), a trigger from the patient, a remote trigger from a physician, etc. The data collection module 402 can measure and store the pulmonary artery (PA) pressure from the pressure sensor 418 positioned in the PA (task 610). The data processing module 404 can determine if the end of the sample period has been reached (task 612). The duration of the time period to obtain the PA pressure can be defined (task 614) (e.g., about two seconds, at the start of an R wave until the end of an R wave, multiple heart beats that are averaged, etc.).

When the end of the sample period has been reached, the data processing module 404 can identify the PA systolic and diastolic pressures (as shown in FIG. 3) during the sample period (task 616). The data processing module 404 can determine whether all the pressure values are within their physiological ranges (task 618), for example, to identify noise and/or artifacts. If the values are not within their physiological ranges, the process 600 can throw out the pressure values for the sample period (task 620) and return to the start of the ischemia detection (task 608).

If the values are within their physiological ranges, the data processing module 404 can compare the pressure values to the baseline values (task 622) that were previously measured and stored (task 606). The data processing module 404 can then determine whether the PA diastolic pressure increased beyond a threshold (task 624) (e.g., about 25-50% beyond the baseline value or preferably about 33% beyond the baseline value). If no, the data processing module 404 can determine whether the PA systolic pressure decreased beyond a threshold (task 626) (e.g., about 25-50% beyond the baseline value or preferably about 33% beyond the baseline value).

The data collection module 402 can measure complementary sensors (task 630) that include one or more of the following: heart rate, heart rate variability, number of premature ventricular contractions (PVC's), non-sustained ventricular tachycardia (NSVT), sustained ventricular tachycardia (SVT), time of day, electrocardiogram, patient activity, core body temperature, intra-cardiac impedance, intra-thoracic impedance, respiration rate, mixed venous oxygen saturation, wall contractility, wall tension, heart sounds, pulse oximeter, and pulse pressure.

If the PA systolic pressure did decrease beyond a threshold (task 626), the data processing module 404 can determine whether the data from the complementary sensors confirms ischemia (task 628). If yes, the process confirms ischemia in the RV (task 632). If the PA systolic pressure did not decrease beyond a threshold (task 626), the process 600 can return to the start of the ischemia detection (task 608).

If the PA diastolic pressure did increase beyond a threshold (task 624), the data processing module 404 can determine whether the PA systolic pressure also increased beyond a threshold (task 634) (e.g., about 25-50% beyond the baseline value or preferably about 33% beyond the baseline value). If yes, the process 600 can confirm ischemia in the LV (task 636). If no, the data processing module 404 can determine whether the PA systolic pressure decreased beyond a threshold (task 638) (e.g., about 25-50% beyond the baseline value or preferably about 33% beyond the baseline value). If yes, the data processing module 404 can determine whether the data from the complementary sensors confirms ischemia (task 640). If yes, the process 500 can confirm ischemia in the LV (task 636).

If the PA systolic pressure did not decrease beyond a threshold (task 638), the process 500 can return to the start of the ischemia detection (task 608). If the complementary sensors did not confirm ischemia (task 640), the process can also return to the start of the ischemia detection (task 608).

As shown in FIG. 11, process 700 is an alternative embodiment of the process 500 in which pressure is measured in the RV. The process 700 includes triggering the data collection module 402 to measure baseline hemodynamic values (task 702). The accelerometer 419 or other methods can be used to determine if the patient is at rest (task 704). If the patient is not at rest, the process 700 can wait until the patient is at rest. If the patient is at rest, the data collection module 402 can measure and store baseline hemodynamic values (task 706) (e.g., for about one hour or another suitable time period). In some embodiments, baseline waveforms can be collected with a suitable monitoring device, such as a monitoring device including a mechanical sensor capable of detecting a pressure signal from inside the right ventricle of the heart. In some embodiments, the suitable monitoring device can be used to obtain the pressure signals 300 and to extract the dP/dt signal 302, as shown in FIG. 3.

Process 700 includes triggering the start of ischemia detection (task 708), which can include a trigger signal from the ECG 414, a trigger based on a time period (e.g., about every five minutes), a trigger from the patient, a remote trigger from a physician, etc. The data collection module 402 can measure and store the ventricular pressure from the pressure sensor 418 positioned in the RV (task 710). The data processing module 404 can determine if the end of the sample period has been reached (task 712). The duration of the time period to obtain the ventricular pressure can be defined (task 714) (e.g., about two seconds, at the start of an R wave until the end of an R wave, multiple heart beats that are averaged, etc.).

When the end of the sample period has been reached, the data processing module 404 can identify the systolic and diastolic pressures (as shown in FIG. 3) during the sample period (task 716). The data processing module 404 can calculate dP/dt during the sample period (task 718). The data processing module 404 can determine whether all the pressure values are within their physiological ranges (task 720), for example, to identify noise and/or artifacts. If the values are not within their physiological ranges, the process 700 can throw out the pressure values for the sample period (task 722) and return to the start of the ischemia detection (task 708).

If the values are within their physiological ranges, the data processing module 404 can compare the pressure values to the baseline values (task 724) that were previously measured and stored (task 706). The data processing module 404 can then determine whether the maximum relaxation dP/dt value decrease beyond a threshold (task 726) (e.g., about 25-50% beyond the baseline value or preferably about 33% beyond the baseline value).

The data collection module 402 can measure complementary sensors (task 730) that include one or more of the following: heart rate, heart rate variability, number of premature ventricular contractions (PVC's), non-sustained ventricular tachycardia (NSVT), sustained ventricular tachycardia (SVT), time of day, electrocardiogram, patient activity, core body temperature, intra-cardiac impedance, intra-thoracic impedance, respiration rate, mixed venous oxygen saturation, wall contractility, wall tension, heart sounds, pulse oximeter, and pulse pressure.

If the maximum relaxation dP/dt did decrease beyond a threshold (task 726), the data processing module 404 can determine whether the data from the complementary sensors confirms ischemia (task 728). If yes, the process confirms ischemia in the RV (task 732). In addition, the data processing module 404 can determine whether the ePAD value increased beyond a threshold (task 736) (e.g., about 25-50% beyond the baseline value or preferably about 33% beyond the baseline value). If yes, the process 500 can also confirm ischemia in the LV (task 738).

If the maximum relaxation dP/dt did not decrease beyond a threshold (task 726), the data processing module 404 can determine whether the maximum contraction dP/dt increased beyond a threshold (task 734). If yes, the process 700 can measure the patient's level of exertion and/or activity (task 740), e.g., based on the heart rate 416, the accelerometer 419, the temperature sensor 430, respiration data, pressures, etc. The data processing module 404 can then determine whether the increase can be explained by exertion (task 742). If yes, the process 700 can return to the start of the ischemia detection (task 708). If no, the data processing module 404 can determine whether the data from the complementary sensors confirms ischemia (task 744). If yes, the process confirms ischemia in the LV (task 738). If no, the process can return to the start of the ischemia detection (task 708).

While at least one example embodiment has been presented in the foregoing detailed description, it should be appreciated that a vast number of variations exist. It should also be appreciated that the example embodiment or embodiments described herein are not intended to limit the scope, applicability, or configuration of the present disclosure in any way. Rather, the foregoing detailed description will provide those skilled in the art with a convenient road map for implementing the described embodiment or embodiments. It should be understood that various changes can be made in the function and arrangement of elements without departing from the scope of the present disclosure as set forth in the appended claims and the legal equivalents thereof.

The invention claimed is:

1. An implantable medical device comprising:
   an implantable pressure sensor providing a signal indicative of a patient's blood pressure;
   a data processing module coupled to the pressure sensor, the data processing module configured to determine a blood pressure rate of change based on the blood pressure signal;
   the data processing module configured to identify at least one of impaired relaxation and impaired contractility based on a maximum value of the blood pressure rate of change and to detect ischemia in response thereto; and
   a therapy module comprising a pacing electrode coupled to the data processing module and configured to deliver therapy to the patient responsive to the identification of one of impaired relaxation and impaired contractility.

2. The device of claim 1 wherein the maximum value comprises maximum rate of pressure increase.

3. The device of claim 1 further comprising an implantable transmitter coupled to the processing module and providing a transmission responsive to the identification of one of impaired relaxation and impaired contractility.

4. The device of claim 1 wherein the data processing module is further configured to activate the pressure sensor to obtain the indicative signal therefrom over a defined sample period.

5. A method of delivering a therapy to a patient, comprising:
   employing a pressure sensor implanted in the patient to provide a signal indicative of a patient's blood pressure;
   employing a processing module implanted in the patient and coupled to the pressure sensor to determine a maximum value of blood pressure rate of change from the blood pressure signal;
   employing the implanted processing module to identify at least one of impaired relaxation and impaired contractility based on the maximum value of the blood pressure rate of change and to detect ischemia in response thereto; and
   employing a therapy module comprising a pacing electrode implanted in the patient and coupled to the processing module to deliver therapy to the patient responsive to the identification of one of impaired relaxation and impaired contractility.

6. The method of claim 5 wherein the pressure sensor is located in one of the left ventricle, the right ventricle, the left atrium, and the pulmonary artery.

7. The method of claim 6, further comprising obtaining a complementary signal comprising at least one of the patient's: heart rate, heart rate variability, time of day, heart sounds, patient activity, impedance, core body temperature, respiration rate, mixed venous oxygen saturation, wall contractility, wall tension, pulse oximetry, pulse pressure, number of premature ventricular contractions, non-sustained ventricular tachycardia, and sustained ventricular tachycardia.

8. The method of claim 7 wherein the processing module analyzes the blood pressure signal and the complementary signal to determine if the pressure signal represents a normal hemodynamic response.

9. The method of claim 5 wherein the maximum value comprises maximum rate of pressure increase.

* * * * *